Figure 1:
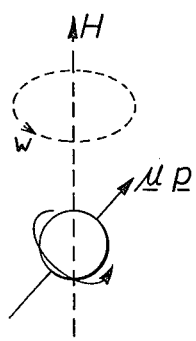

United States Patent [19]

Moore et al.

[11] Patent Number: 4,475,084

[45] Date of Patent: Oct. 2, 1984

[54] NUCLEAR MAGNETIC RESONANCE DETECTOR

[75] Inventors: William S. Moore, Mapperley Park; Robert C. Hawkes, Bramcote, both of England; Geoffrey N. Holland, Chagrin Falls, Ohio

[73] Assignee: Picker International Limited, Wembley, England

[21] Appl. No.: 337,184

[22] Filed: Jan. 5, 1982

[30] Foreign Application Priority Data

Jan. 15, 1981 [GB] United Kingdom ............... 8101172
Jan. 15, 1981 [GB] United Kingdom ............... 8101173
Feb. 2, 1981 [GB] United Kingdom ............... 8101175
Feb. 2, 1981 [GB] United Kingdom ............... 8101176

[51] Int. Cl.³ .......................................... G01R 33/08
[52] U.S. Cl. ................................... 324/309; 324/307
[58] Field of Search ............... 324/300, 309, 307, 312, 324/318

[56] References Cited

U.S. PATENT DOCUMENTS 4,184,110 1/1980 Hinshaw ........................... 324/300
4,284,948 8/1981 Young ............................... 324/309
4,322,684 3/1982 Hounsfield ........................ 324/309

FOREIGN PATENT DOCUMENTS 2026172 1/1980 United Kingdom .
2037996 7/1980 United Kingdom .
1578910 11/1980 United Kingdom .
2049947 12/1980 United Kingdom .

Primary Examiner—Michael J. Tokar
Attorney, Agent, or Firm—Cahill, Sutton & Thomas

[57] ABSTRACT

Method and apparatus for producing an N.M.R. picture of a plane through an object by isolating the plane using an oscillating gradient and interrogating the plane using a rotating gradient and a multiplicity of R.F. pulses which are averaged over a defined period to produce an average response which is used to produce the N.M.R. picture.

7 Claims, 20 Drawing Figures

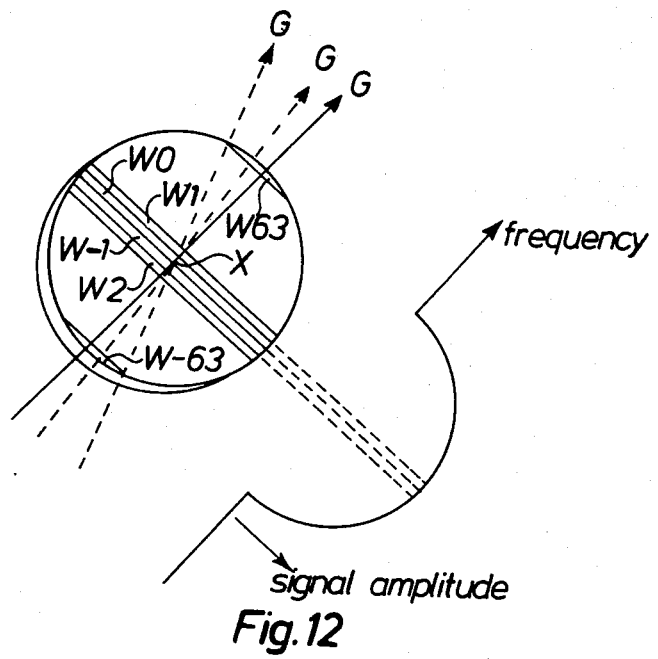
Fig. 12
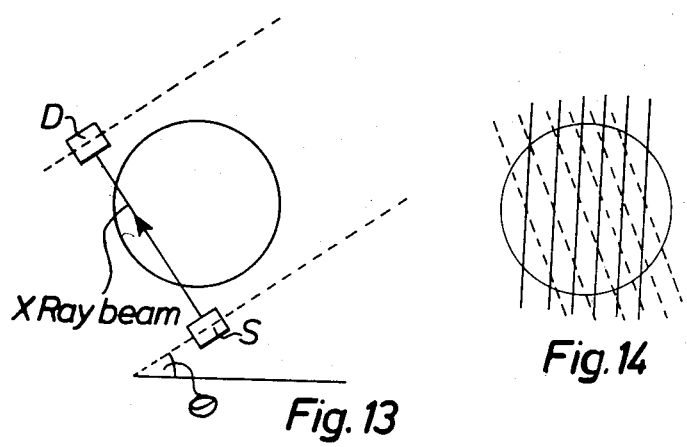
Fig. 13
Fig. 14

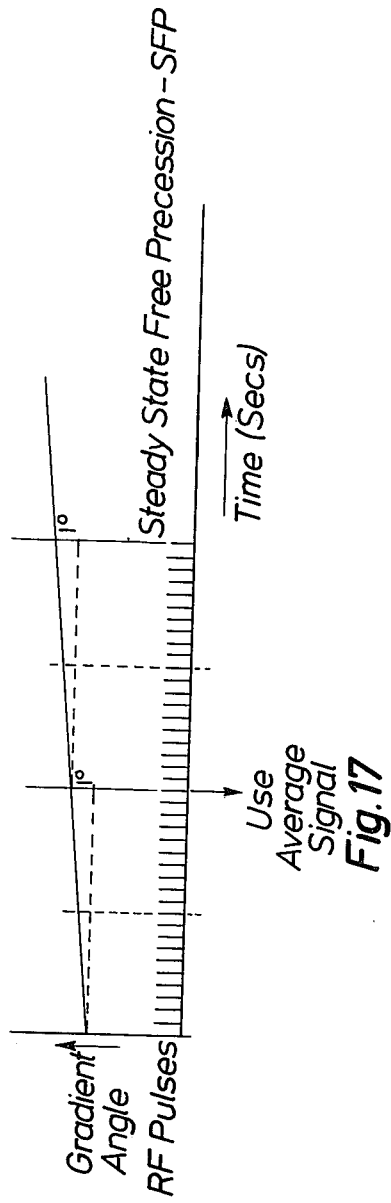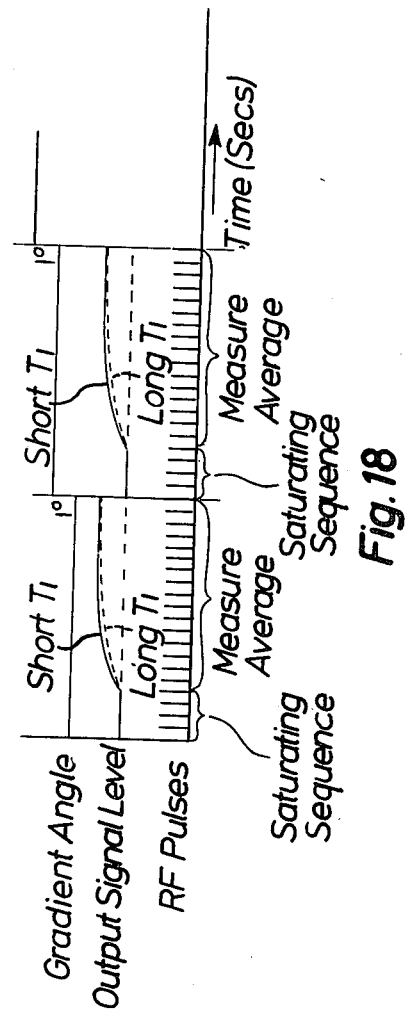

NUCLEAR MAGNETIC RESONANCE DETECTOR

The present invention relates to Nuclear Magnetic Resonance (N.M.R.) detection methods and apparatus and more particularly to the production of an N.M.R. image of a plane through an object.

N.M.R. detection techniques are useful in a number of different fields. A particular application is found in the detection of substances within a body, which substances are not detectable by normal X ray techniques. This may occur either because the region in which the substance is present is within a wall structure which is impenetrable by X rays or that the substance itself is not sufficiently different in density from the surroundings to be distinguished on an X ray photograph.

It is an object of the present invention to produce an N.M.R. image of a plane through an object thus allowing an analysis to be made of the substances within such a plane.

It is also an object of the present invention to be able to vary the plane through the object thus enabling an analysis of the object by examination of various planes through the object.

According to the present invention there is provided a method and an apparatus for producing an N.M.R. a picture of a plane through an object in which the object is subjected to a high constant magnetic field, to an oscillating field the intensity of which varies across the object except at a selected plane where the oscillating field is substantially zero and to a magnetic field having a gradient in the selected plane the orientation of which may be varied in accordance with a set program. At each position of orientation of the gradient magnetic field, the object is subjected to multiple pulses of R.F. frequency magnetic radiation including an initial sequence of pulses which saturate the N.M.R. response. The resulting N.M.R. responses following the initial sequence of pulses are averaged and recorded from each position, and a picture of the total N.M.R. response within the selected plane is obtained by operating on the recorded responses.

Figure 3:
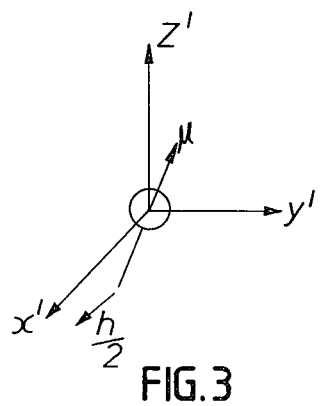
Figure 2:
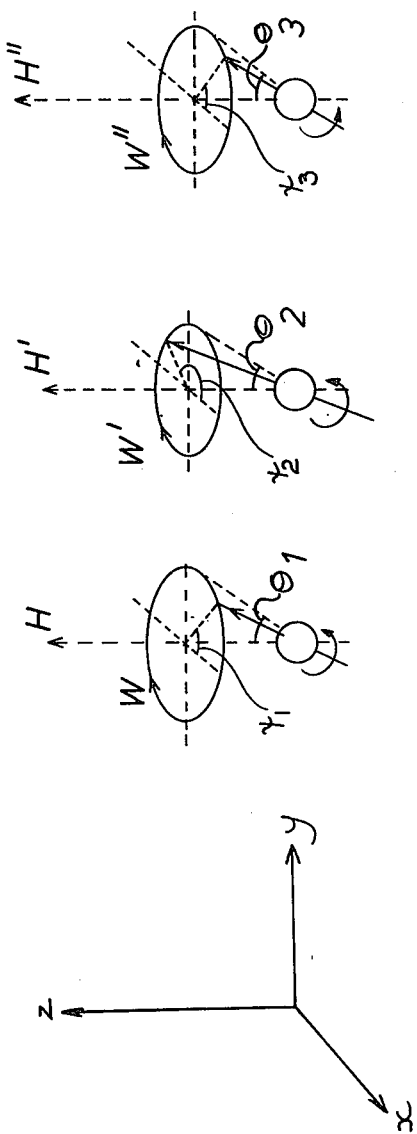
Figure 4:
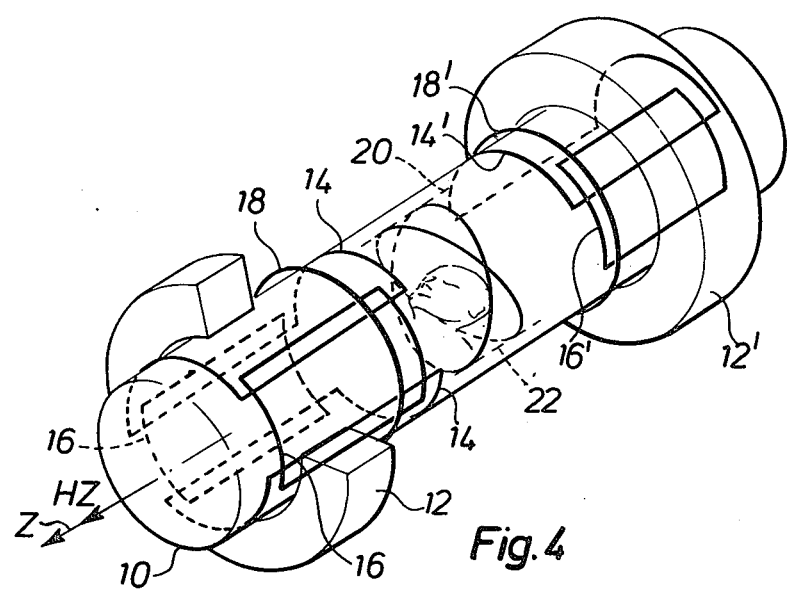
Figure 5:
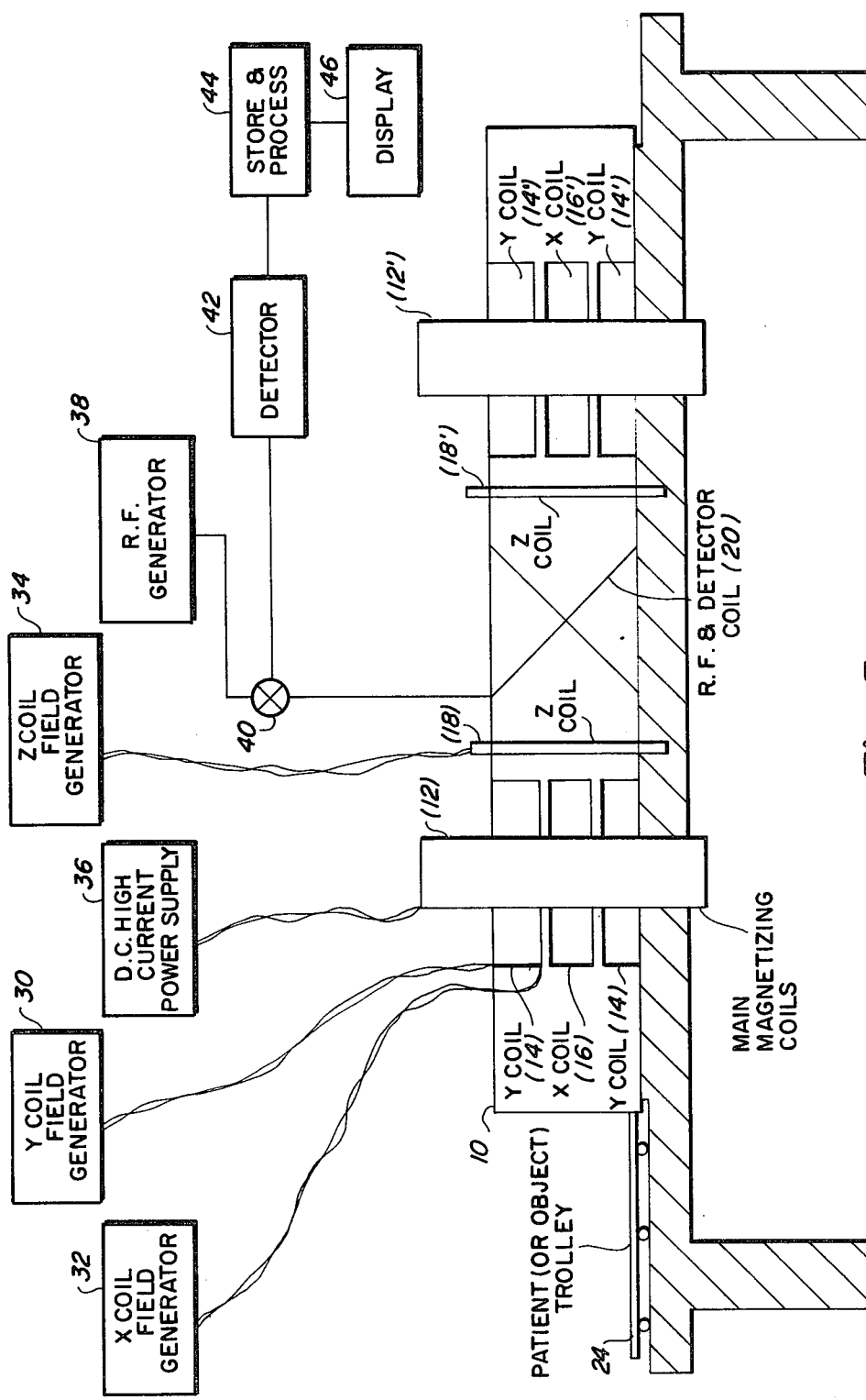
Figure 6:
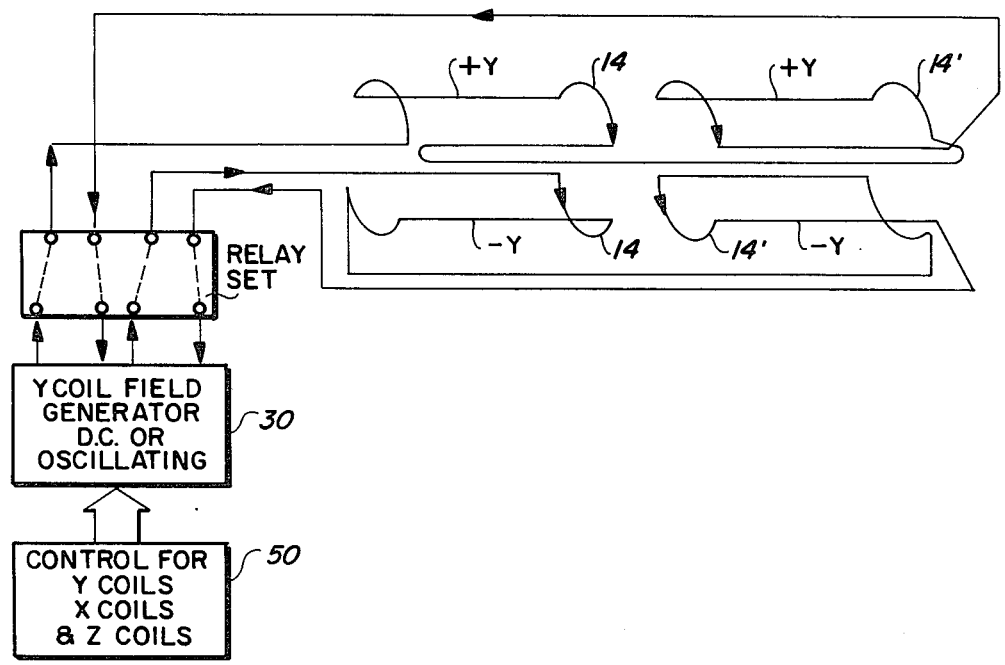
Figure 7:
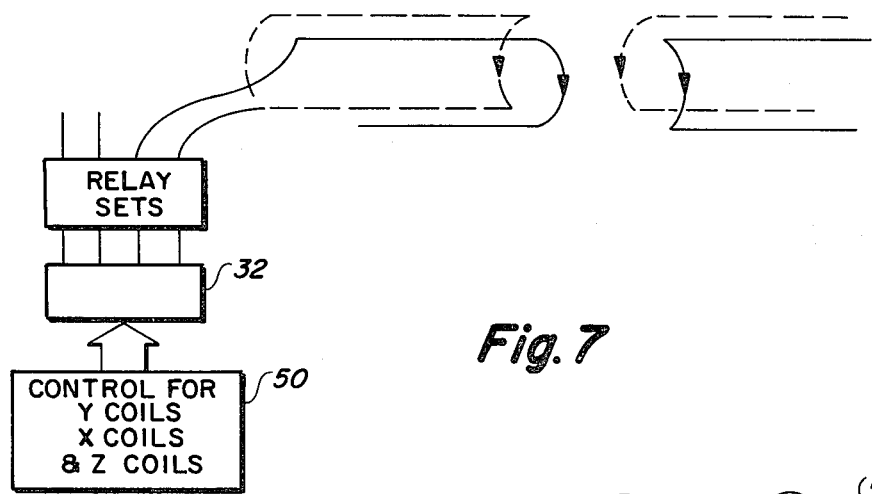
Figure 8:
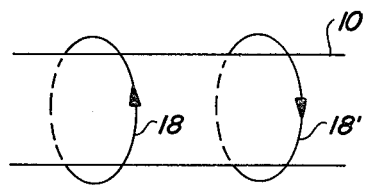
Figure 9:
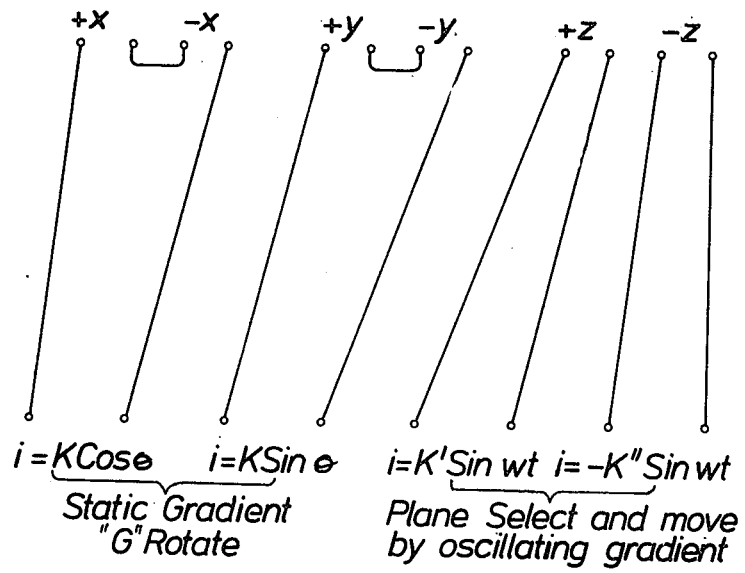
Figure 10:
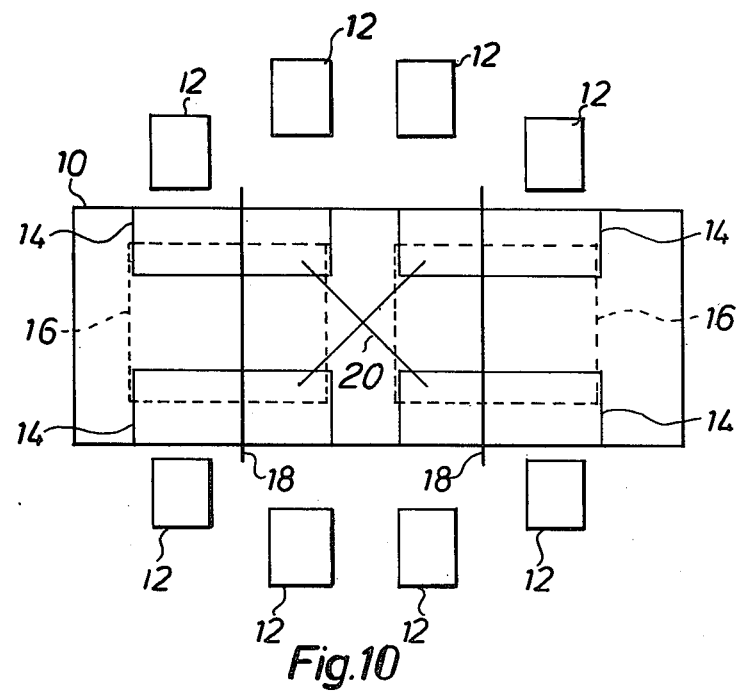
Figure 11:
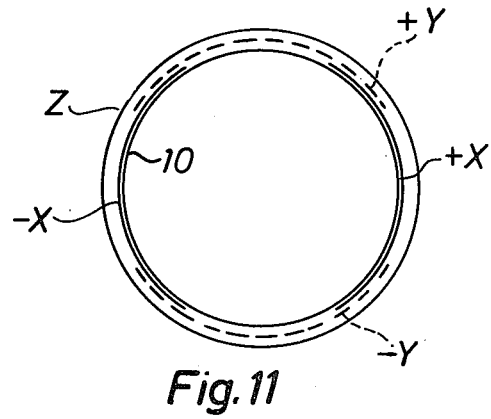
Figure 15:
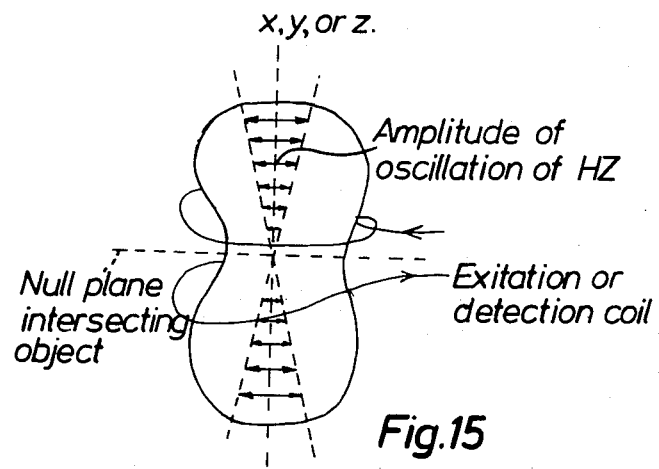
Figure 16:
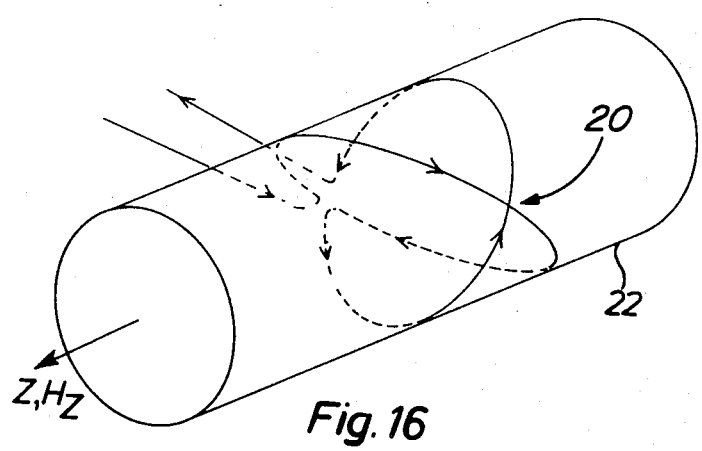
Figure 19:
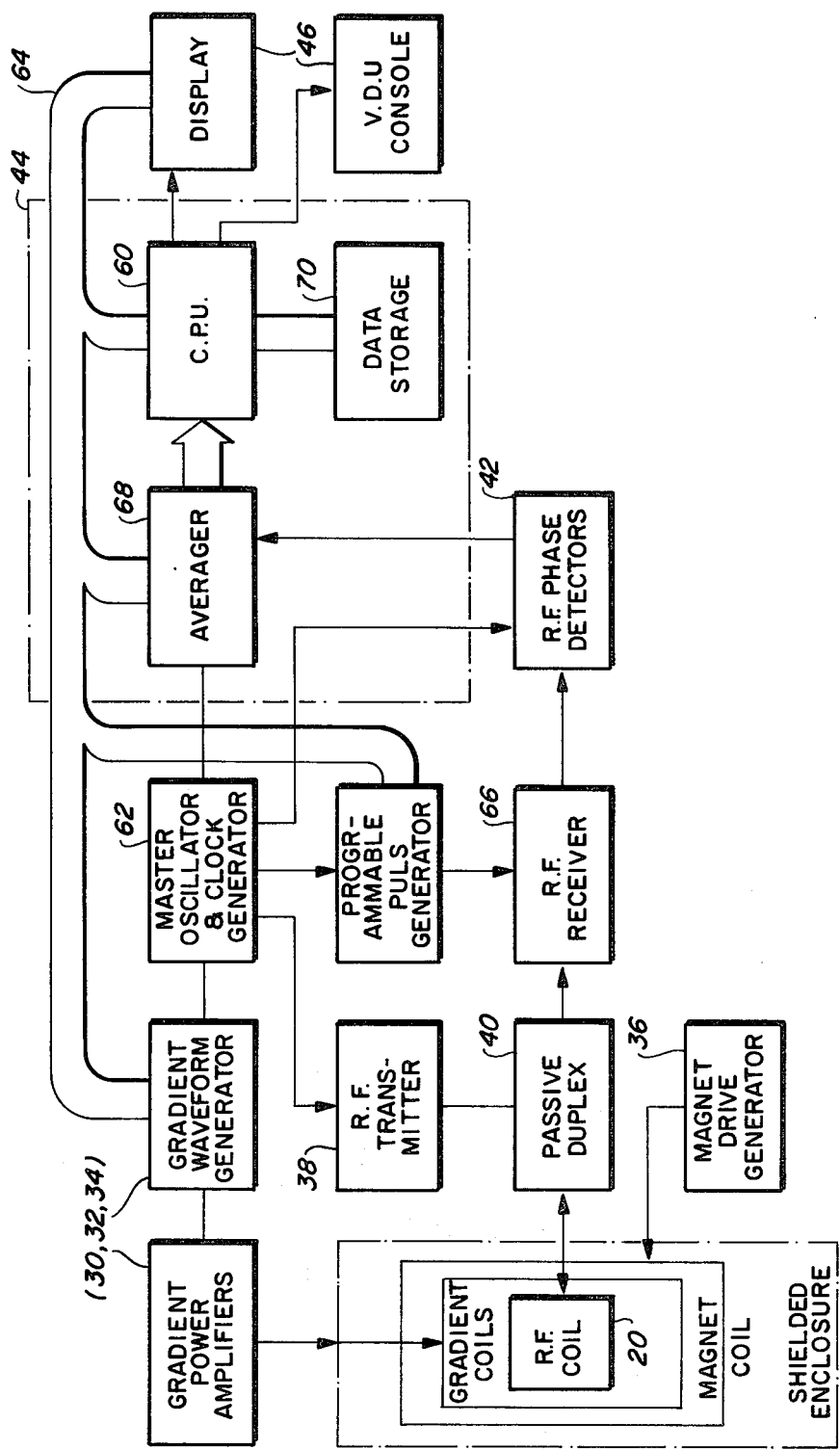
Figure 20:
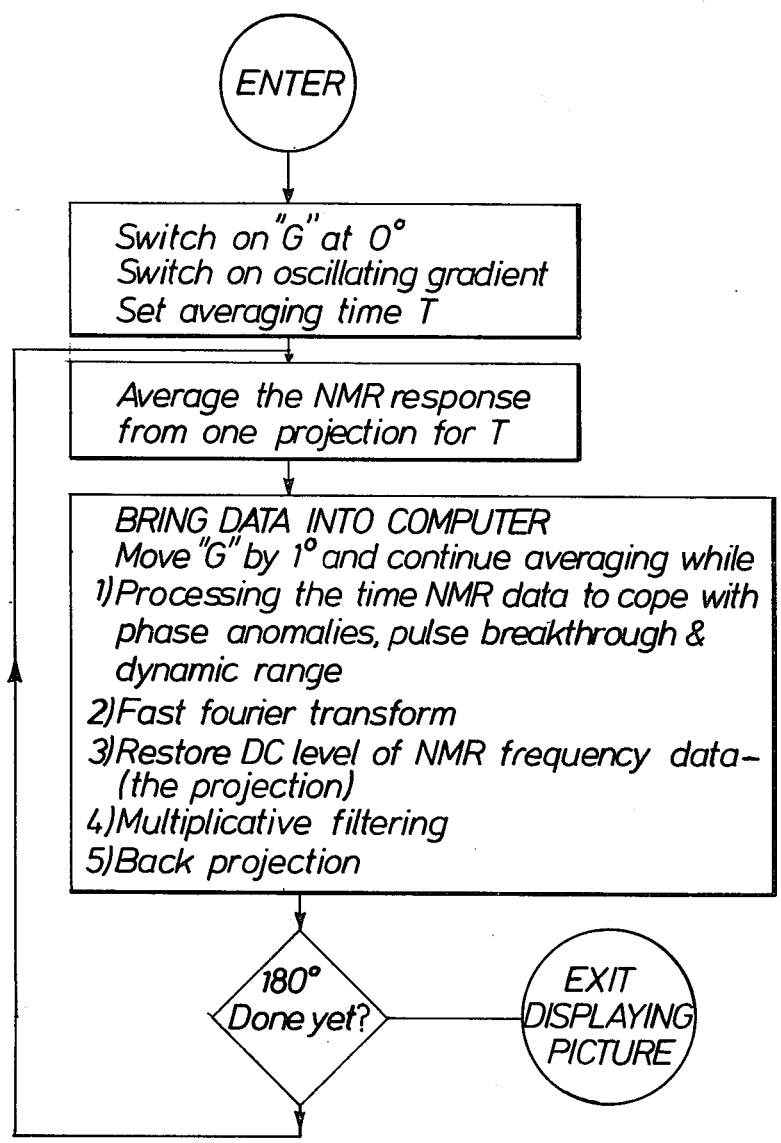

Embodiments of the present invention will now be described with reference to the accompanying drawings in which:

FIG. 1 shows a single isolated nucleus and is used herein to describe the known N.M.R. detection techniques, FIG. 2 shows an instantaneous "snapshot" of three nuclei precessing in a field with a gradient in the y direction, FIG. 3 shows a single isolated nucleus illustrating the x', y' and z' axis in relation thereto, FIG. 4 shows an N.M.R. imaging apparatus in accordance with the present invention, FIG. 5 shows a schematic side view of the apparatus of FIG. 4. showing the major features, FIG. 6 shows a possible connection pattern for the ycoils of the apparatus of FIG. 4 and the coil field generator, FIG. 7 shows in a more simplified form for the x coils the direction of current flow in the coils, FIG. 8 shows the direction of current flow in the z gradient coils, FIG. 9 shows the coil connections and signal generator connections for isolation of a transverse plane, FIG. 10 shows the coils in cross sectional elevation in a practical embodiment, FIG. 11 shows the position and relative size of the x, y, z coils in a cross section through the longitudual axis of the apparatus, FIG. 12 shows a cross section through a body undergoing N.M.R. imaging in the apparatus of FIG. 4 illustrating the technique of isolation of the required image plane, FIG. 13 shows for explanation the known techniques for constructing an X ray image of a plane within an object, FIG. 14 shows two successive projections for constructing the X ray image, FIG. 15 shows an object under examination in the apparatus of FIG. 4 illustrating plane selection by an oscillating field, FIG. 16 shows an R.F. coil suitable for the N.M.R. apparatus shown in FIG. 4, FIG. 17 shows a first pulse sequence for interrogation of a section within a selected plane, FIG. 18 shows a second pulse sequence for interrogation of a section within a selected plane, FIG. 19 shows a blopck diagrammatic form the electrical circuitry for the apparatus of FIG. 4, and FIG. 20 shows a flow diagram of the program sequence for the electrical circuitry of FIG. 19.

The invention will be described commencing with a brief explanation of the basic principles of N.M.R. detection technique.

The most useful operational description of N.M.R. that has been given so far is by a set of equations due to Bloch. These equation attempt to quantify the total magnetic behaviour of a collection of magnetic gyroscopes (nuclei) subjected to time varying and static magnetic fields. The behaviour of a single isolated nucleus of magnetic momement $\mu$ is that of a gyroscope i.e. it precesses at a frequency w (the LARMOR FREQUENCY) dependent on the mechanical couple that it experiences due to an applied magnetic field of magnitude H. The size of the couple is given by $\mu \wedge H$ and its sense is such as to continually try to align the moment $\mu$ with the field H. The Lamor frequency $w = \gamma \cdot H$, and the precession is about the applied magnetic field direction (FIG. 1). This motion is completely described by the classical equation relating angular momentum p and couple (or torque) $\mu \wedge H$ viz $dp/dt = \mu \wedge H$. However $p = \mu/\gamma$ and so one can write $du/dt = \gamma\mu \wedge H$ i.e. the angular momentum p of a given nucleus is related to its magnetic moment $\mu$ by the magneto—gyric ratio which is a constant for a given species of nucleus, and which differs for different magnetic nuclear species. All nuclei such as hydrogen nuclei, or protons are identical and have the same $\gamma$ and it would seem therefore that the total magnetic moment M of a collection of protons (say) would be given by $M = \epsilon\mu$ and so one could write $dM/dt = \gamma M \wedge H$. However there are three further physical effects that Bloch had to add namely:

1. that the collection of identical nuclei placed in a magnetic field (conventionally always along the Z axis) magnetize in the Z direction only i.e $M_Z$ is finite and equal to Mo when the system is in thermal equilibrium.
2. that if the system is not in thermal equilibrium, it will get there eventually, and usually approach equilibrium in an exponential fashion with characteristic time $T_1$, the longitudinal or 'spin-lattice' relaxation time. By 'lattice' is meant the system, describable by a temperature that the nuclei are trying to come to equilibrium with.

3. that if there is any net magnetization Mx or My perpendicular to the steady field direction and due to the sum of the perpendicular components $\mu x$, $\mu y$ of each elementary magnet's motion, then this will in general tend to disappear as they do not all precess at precisely the same frequency, since if for no other reason they all interact with each other in a random way in a given material. This effect he also describes in terms of an exponential identical disappearance of Mx and My with characteristic time $T_2$, the transverse or 'spin-spin' relaxation time.

Thus finally the Bloch equations for the total magnetization of a collection of nuclei which is the quantity that couples to coils and induces observable voltages, are $$dMz/dt = [\gamma(Mx \cdot Hy - My \cdot Hx)] - (Mz - Mo)/(T_1)$$

$$dMx/dt = [\gamma(My \cdot Hz - Mz \cdot Hy)] - (Mx)/(T_2)$$

$$dMy/dt = [\gamma(Mz\, Hx - Mx\, Hz)] - (My)/(T_2)$$

The terms in square brackets describe the action of magnetic fields, precession etc., and the terms in brackets the action of relaxation i.e. the system of nuclei by virtue of its internal interactions and coupling to a thermal reservoir (solid, liquid etc.), tries to attain equilibrium in which case $Mx = My = 0$ and $Mz = Mo$ as can easily be seen.

The complications that arise when trying to observe and understand systems of finite spatial extent containing many identical nuclei when they are subjected to static and time-varying fields, which arise in both laboratory analytical N.M.R. and N.M.R. imaging therefore involve visualizing the solution of these fundamental equations when $H_{x, y, z}$ can be complicated functions of both time and space.

ity. Typically $H_z$ varies over the sample volume by less than 1 part in 10.

Lauterbur realized in 1973 that this spatial coding of NMR signals by frequency, when a sample was placed in a field gradient, could be used to produce NMR 'maps' or 'images' of samples having non-uniform NMR properties.

The proton or hydrogen nucleus has been extensively used, because of its large magnetic moment and abundance in water, to make NMR images. The main use of such imaging techniques is in the medical field, following Damadian's suggestion, and the measurements of others, that the NMR characteristics of cancerous tissue differ from the surrounding normal tissue, and the realization that bio-chemical changes, mechanical obstructions to flow and abnormal flow of proton-containing materials such as blood are all visualizable by NMR. There are other applications particularly in the area of water flow in porous building and structural materials, soil and the like, and in the detailed mechanism of the uptake of water or its loss by natural (i.e. food) products.

NMR images are representations of the NMR signal coming from different volume elements within say a plane of finite thickness through an object. The 'size' of the NMR signal from a given volume element is represented by the brightness of the associated picture element in a 2D representation of the particular plane through the object on a display device. The 'size' of the NMR signal from a volume element depends in a complicated way on the mode of excitation and detection of the NMR and on the precise method of obtaining the 'image' of say a plane. In the most general case the 'size' of the NMR signal from a volume element, hence the brightness of the particular associated picture element depends on:

| | |
|---|---|
| A | The number of nuclei present in the object volume element. |
| B $T_1$ and | which themselves depend on the microscopic molecular motion of the nuclei in their molecules. Roughly speaking, mobile liquids have $T_2 = T_1$ (about 2 sec for water protons) and have $T_2 << T_1$ ($T_2 \approx 30\,\mu$ sec $T_1 = 60\,\mu$ sec for protons in ice) N.B. $T_2$ can never be greater than $T_1$. |
| C $T_2$ | |
| D | Whether or not nuclei in an object volume element fixed in space are flowing through the volume element or in oscillatory motion during the measuring time. It can easily be seen for example that if a fluid volume element is flowing along a magnetic field gradient, then the NMR signal it is emitting is continually changing in frequency. |

For our purposes, there will always be a large static magnetic field $H_z$ (typically 0.1 Tesla), there will be occasional bursts of small amplitude radio frequency fields $h_x$ and $h_y$ (typically $10^{-4}$ Tesla and note perpendicular to the static field), and there will be both static and time-varying small field gradients Gx, y, z, i.e. spatial variations of the total field $H_z$ in the x, y, z co-ordinate directions, assumed linear (typical $Gx = 10^{-4}$ Tesla/cm, then for an object of x-extent 20 cm, the field variation across it is $2 \times 10^{-3}$ Tesla). These gradients are produced by subsidiary coils (gradient coils) which are separate from the main or z—field—producing coils.

The effect of gradients is to code the NMR signal in space via the precession frequency, which depends on the total magnetic field at a given position in space. This latter realization has led to the production of magnets to produce Hz which have very good spatial homogene- To form an NMR image it is firstly necessary to provide RF excitation of the object and to detect the resultant NMR signal. The equilibrium nuclear magnetic system in an extended object can be excited by 'resonant' RF pulses applied at or near the Larmor frequency. This is done by wrapping a coil around the object of a suitable design so that there is an oscillatory RF magnetic field present of amplitude h in the x direction at right angles to $H_z$, and uniform over the sample. This field h can be thought of as the sum of two rotating fields in the xy plane of amplitude h/2. The field rotating in the opposite sense to the nuclear precession (due to Hz) can be neglected, whereas the field rotating in the same sense and almost synchronous with the nuclear precession interacts strongly with the precessing nuclear moments and causes their precessional angles $\theta$ (FIG. 2) to increase so long as the pulse is applied, as can be seen by the following argument. Imagine yourself in a set of axes x' y' z' which rotate at angular velocity w about the original laboratory z axis, about which is precessing a single nucleus, also at w. In the 'rotating frame' of reference you will observe a stationary nuclear moment $\mu$, aligned almost along the z' axis if the system is almost in equilibrium. Therefore in the rotating frame there appears to be no effective magnetic field H'. Since the moment $\mu$ is not precessing, w'=0 therefore H' must be zero since w'=$\gamma$H' and $\gamma$ is unaltered. The rotating RF field component h/2 at w and in the same sense of rotation as $\mu$ will also be stationary in the rotating frame. Thus the moment $\mu$ must precess about h/2, the x direction in FIG. 3, in exactly the same way as $\mu$ precesses about $H_z$ in the normal stationary laboratory frame of reference. Thus if $\mu$ starts off in the Z' direction, it precesses in the z' y' plane about the x' axis at the comparatively slow rate $\Omega=\gamma h/2$ (since h/2 < <$H_z$). If the RF pulse is switched on for a certain time then all the moments $\mu$ (which are originally along the z' direction in equilibrium) will turn through the same angle $\theta$, the RF pulse is then said to be a '$\theta$-pulse'. Note that a '90° pulse' will therefore turn all the nuclei to the y' direction from the z' direction and that further-more, the moments will all be aligned initially along y' with a large resultant magnetization $M_o$.

If we now transform back to the laboratory frame of reference, what we have found is that immediately following a 90° pulse, all the nuclear moments will be aligned, somewhere in the x y plane depending on the number of times they have precessed during the RF pulse of length $\tau$, around the Z axis due to $H_z$. Thus we have created a large resultant moment $M_o$ in the x y plane. Provided the 90° pulse length was short compared to the dephasing time $T_2$ of the moments $\mu$ about z, then following the 90° pulse, the resultant total moment will precess about z at w (=$\gamma$ Hz) and die away as the individual nuclear moments dephase with characteristic time $T_2$. The initial moment Mo, along z will slowly reappear with in general a different characteristic time $T_1$.

The above is a description of pulsed NMR techniques where the signal following say a 90° pulse can be detected by the voltage induced in a second (or it can be the same) RF coil by the rotating magnetic moment M precessing at right angles to the steady field Hz. This signal is known as the FREE INDUCTION DECAY or FID. Clearly the receiver coil, if it is not the same coil as that used to excite the nuclear system, must also be sensitive to magnetization M in the transverse or xy plane, and it is usual to have its magnetic axis crossed with that of the exciting coil, i.e. in the y direction, to minimize pick-up of the exciting pulses in the receiving system. This latter is a serious problem in all pulsed NMR, because the RF pulse oscillating voltage across the high Q excitation coil necessary to make $\tau$, the 90° pulse length sufficiently short compared to the $T_2$ of many systems can be several kilovolts, whereas the induced nuclear signal in the receiving coil is of order nanovolts. Minimization of receiver 'paralysis' by the exciting pulse is a difficult problem, and has an exact analogue in radar, where a high-power emitted pulse is almost immediately followed by a weak echo signal that must be detected. In the apparatus according to the present invention shown in FIG. 4 patients lie along the Z axis of a tube 10 placed coaxially within large solenoid coils 12, 12' which produce the large constant magnetizing field Hz in the z axis direction. Three further sets of coils 14, 16 and 18 are wound round the tube 10 at one end. Each of the coils 14 and 16 are wound and then placed on to the outside surface of the tube 10 in the manner of a saddle. Taking coil 16 as an example the coil is shown as a single wire but will in practise be multi-turn. The coils, 14, 16 are basically rectangular in shape and the one side of the rectangular coil 16 is hidden in the construction by the tube 10 and is shown dotted. The coil 18 is cylindrical in shape and wound circumferentially round the tube 10.

At the other end of the tube 10 three further sets of coils 14', 16' and 18' are positioned. For clarity, and because the majority of the second coil of each of the pairs 14' and 16' is hidden behind the tube 10 only one coil of each pair is shown. The arrangement of the coils at either end is identical.

The coil pairs 14, 16 and 18 and 14', 16' and 18' are arranged to leave a portion of the tube 10 open in the centre.

At this position within the tube 10 the object to be examined is placed. An exciter and receiver coil 20 is placed within the tube 10 on a cylindrical former 22.

In the preferred embodiment the object to be examined is the head of a person. The person is supported within the tube 10 by means of a trolley 24 (shown in FIG. 5) which preferably is slideable within the tube 10 to allow the person to be placed on the support external to the tube and to be slid along the tube to a desired position.

Referring now to FIG. 5 the apparatus of FIG. 14 is shown in a schematic elevation view to illustrate the shape of the coils and to shown the major electrical drive generators for the coils. As in other figures reference numerals are retained for the features present in several figures.

The Y field coils, 14, 14' are supplied with energising current from a generator 30 and similarly the X and Z coils are supplied from generators 32, 34. The current can be D.C. or oscillating as selected.

The main magnetising field coils 12, 12' are supplied with current from a D.C. high current power supply 36.

The R.F. and detector coil 20 is supplied with pulsed R.F. current from an R.F. generator 38 via an isolating gate 40. This gate serves to isolate the R.F. "transmitted" pulse to the coil 20 from the "received" pulse detected by the coil 20 in its subsequent role as detector. The detected N.M.R. response is fed to a detector and amplifier 42 the outputs of which are digitised and stored in appropriate locations within a store 44 to enable the subsequent data processing to display the picture on a display 46. A more detailed description of the electrical circuitry is given hereinafter with reference to FIGS. 19 and 20.

Referring now to FIG. 6 a possible connection pattern for the Y coils 14, 14, 14', 14' is shown. Again as previously mentioned it is stressed that although for simplicity the coils are shown as single turns they will normally be multiple turn coils.

The important feature shown by FIG. 6 is the direction of current in the coils at the operational ends i.e. the ends between which the object to be examined is placed.

The current through the coils is controlled by the generator 30 which is controlled by a control system 50 which also controls the current in the X and Z coils to produce the fields necessary to produce the N.M.R. picture of a plane through an object as described hereinafter. With reference to FIG. 7 the direction of current in the X coils 16, 16, 16' and 16' is shown and the connections though not shown may be similar to those for the Y coils of FIG. 6. The X coils are similarly supplied with current from a generator 32 controlled by the control 50.

The connection between the control system 50 and each generator 30, 32, and 34 (for the Z coils) is shown as a multiple connection because it is required to control both magnitude and direction of the current in each coil and also whether the current is D.C. or oscillating.

FIG. 8 shows the direction of current in the Z coils which are supplied as shown in FIG. 5 by a generator 34 also controlled by the control system 50.

The control system 50 gives signals to the generators 30, 32 and 34 to enable the N.M.R. picture of a plane to be formed.

The Y coils are shown connected as an upper pair and a lower pair. These can both be supplied with the same current or can be provided with different oscillating currents to move the plane. When supplied with D.C. the coils will all be supplied with the same current but when used to isolate the plane and supplied with oscillating currents they can be connected independently as shown and supplied with different currents.

The X coils are operated in an connected in an identical manner. Thus at any time two of the coils are driven with DC current and connected in series and one is supplied with an oscillating current and each half of the coils may be supplied with different currents depending on the chosen plane.

An example of the connections showing a transverse plane is shown in FIG. 9. In this embodiment the +X coils (i.e. the two coils on the same side of the tube 10) are connected in series with the −X coils and supplied with a current $i = k \cos \theta$ where K is a constant and $\theta$ is varied to vary the gradient G. Similarly the +Y and −Y coils are supplied with a current $i = K \sin \theta$ and are connected in series.

In contrast however for plane select and plane movement one of the sets of coils must be supplied with an oscillating gradient. In this case it is the Z coils and they are connected separately to each other, one coil +Z to a current $i = K' \sin \omega t$ where K' is a constant not necessarily equal to K; and the other coil −Z to a current $i = K'' \sin \omega t$, where K'' is a constant not necessarily equal either to K or K'.

Obviously to select a plane in a direction orthogonal to that selected in FIG. 9 the Z coils +Z and −Z would be connected in series and supplied with a current $i = K \cos \theta$ (or $K \sin \theta$) and one of the X or Y pairs would be disconnected and fed with $i = K' \sin \omega t$ and $i = K'' \sin \omega t$.

The connections of the coils may be accomplished automatically on selection of a plane by closure of appropriate relays to produce the required interconnections.

Referring now to FIG. 10 there is shown a more accurate geometric drawing of a practical coil arrangement. As can be seen the X and Y coils 14 and 16 "overlap" the sense and R.F. coil 20 and the main magnetising coil arrangement 12 comprises four annular coils arranged approximately in a circle to provide a uniform field in the centre of the sense coil 20.

With reference to FIG. 11 a more accurate geometric arrangement of the coils is shown. Each X and Y coil occupies 120° of arc and overlaps the adjacent Y or X coil by 30°. The coils are wound such that each X, Y and Z coil has the same reluctance and therefore they may be considered interchangeable from the point of view of being driven by the signal generators. This is an extremely practical advantage because of the necessity to change the current generators between the X, Y and Z coils.

In the apparatus of FIGS. 4 to 8 it is possible as described hereinafter to isolate a single plane of finite thickness within the object to be examined by suitable excitation of the coils 14, 16, 18 and 14', 16' and 18'. N.M.R. signals can be extracted from this plane in an unambiguous manner despite the fact that the whole object has been excited by R.F. pulses.

The following description with reference to FIGS. 12, 13 and 14 shows how a picture of the proton nuclei distribution within such a plane can be obtained.

Referring now in particular to FIG. 12 in which the plane is assumed circular and of depth d suppose a one dimensional field gradient G is applied in this plane such that in a strip through approximately the centre of the plane the total magnetic field is unaltered and therefore equal to the steady field Hz. In the positive +G direction the resultant Hz field in successive strips orthogonal to G increases linearly and in the negative (−G) direction the field decreases linearly so that the total N.M.R. response from the plane as sensed by a receiver coil will contain many N.M.R. frequencies from all the strips ($w_{-63} \ldots w_{63}$). The FID following a suitably broadband RF 90° excitation pulse (spanning $w_{-63}$ to $w_{63}$) will thus clearly give a projection of the N.M.R. object on to the gradient direction since each strip of the plane contributes a frequency point on the projection as shown. The Fourier Transformation of the FID of a sample in a linear gradient is the one-dimensional projection of the N.M.R. object on to the gradient direction. If now the gradient G can be rotated through a finite angle, keeping its strength constant, and such that there is a unique point X within the object where for all positions of the gradient G, the total resultant field is unaffected and equal to the applied field, then a larger number of accurate (because of the linearity of G and the existence of X) geometric projections of the N.M.R. object can be obtained from a number of discrete gradient directions.

It is known how to reconstruct an object from a set of linear projections of this type, and this art is the basis of X-ray computerized transgraphy or CT, a medical imaging technique where the projections are obtained by passing a fine X-ray beam through a defined slice, and detecting the beam by a detector D moving simultaneously with the source S as shown in FIG. 13. After each traverse of the source S and detector D the angle $\theta$ is altered and the process repeated to obtain many projections.

Note however that X-ray CT is an ABSORPTION image, not EMISSION as with N.M.R. It is important in projection reconstruction that all parts of the object are examined and contribute to all the projections for the reconstruction process to be predictably accurate. It is also important that at the edge of the object, for successive positions of G, or in the X-ray case for successive directions of the scanning motion that the 'resolution distance' required (or interstrip spacing) should overlap at least to the extent as shown in FIG. 14. These necessary and desirable conditions can be achieved in one embodiment by rotating the gradient G not in discrete steps averaging the N.M.R. signal at each position but CONTINUOUSLY with continuous averaging of the N.M.R. signal. In another embodiment the gradient direction can be moved rapidly from one position to the next followed by a sequence of RF pulses which saturate the N.M.R. signal, so that Averaging for a short period (say 0.5 s) makes the averaged signal more dependent on the recovery time $T_1$. The N.M.R. response is measured during successive intervals as the gradient rotates such that the worst-case N.M.R. frequency change during the averaging interval (at the extreme edge of the object) is less than the interstrip frequency chosen, which corresponds, via the field gradient strength G to the spatial resolution required. (We use 180 or 127 strip frequencies (as indicated in FIG. 12) to span the object, and rotate the gradient G at constant amplitude continuously through 180° whilst taking 128 to 180 interval averages of the projection N.M.R. signal, each therefore averaged over an angular spread of 180/128° or 1°). The means whereby the gradient G is rotated is by using the three sets of gradient producing coils 14, 16, 18 and 14', 16' and 18' wound on the patient support tube which have similar electrical characteristics and which produce uniform gradients (of Hz) in the three (x, y, z) co-ordinate directions. Any pair of these can be selected and driven by cosinuosoidally and sinuosoidally varying currents respectively thus producing a uniformly rotating gradient of constant magnitude in either the xy, yz or zx planes. This facility in conjunction with the slice selection method to be described allows the production of transverse, coronal and sagittal N.M.R. plane images of the human brain. The methods of N.M.R. excitation used during the reconstruction process described above have a considerable bearing on its accuracy and efficacy. It 'multiple-sideband' derived methods are used where the N.M.R. excitation consists of a string of equally-spaced coherent phase alternated RF pulses, then the interstrip frequency clearly corresponds to the RF excitation sideband spacing, and in fact only half of the imaged plane is being examined at any instant. If uniform RF excitation is used, by means of non-periodic pulse excitation sequences then this difficulty can be overcome. There are further problems with multiple-sideband N.M.R. excitation in that not only is the selected plane excited in the applied gradient in a stripwise (though equilibrium) manner by the sidebands, but between the driven equilibrium strips, as can easily be shown, an interleaved stripwise SATURATION phenomenon occurs. (Saturation corresponds to Mx My and Mz all=0). On turning off the RF excitation the N.M.R. system is seriously disturbed from equilibrium and will take a few $T_1$'s to regain it. Thus the multiple sideband method observes only half of the sample at any instant, and even less when the gradient direction is suddenly moved, because then the stripwise equilibrium excitation regions are rotating into the previously saturated strips. However this difficulty can be used to advantage to obtain more $T_1$-dependent signals as described above, by rapid stepwise gradient rotation followed by saturating RF pulse sequences.

A preferred solution is to use alternative pulse sequences with unequally spaced unequal pulses that allow the extent to which the N.M.R. system is away from thermal equilibrium to be carefully controlled, which restores the ability to move the gradient G faster hence produce images in a shorter time. Such sequences also allow the gradient to be rotated in a discrete fashion, and by removing saturation effects, give larger signals. A further major advantage is that by variation of the excitation and averaging sequences in a programmably controllable way, N.M.R. images that exhibit a variable degree of contrast based on varying the influence of the four major N.M.R. parameters mentioned earlier, can be obtained. This will be of great use in determining the usefulness of N.M.R. imaging, particularly proton N.M.R. imaging and more particularly in medical applications. A single oscillatory gradient is used to select the plane, postulated above, within which by reconstruction from N.M.R. projections, N.M.R. images may be produced. The problem here is to select from within a large object, like for instance the human head, a plane, from which signals are exclusively obtained continuously despite the fact that the whole object is excited by RF pulses fed to a coil system, and the detector coil is sensitive to N.M.R. occurring throughout the object. The method used could be called 'selective saturation' and it depends for its success on the combined effect of the pulse sequences and the effect of one oscillating gradient. The detailed form of RF pulse excitation used is unimportant provided the pulse angles are not all much less than 90°. The oscillating gradient is such that there is a plane in space in which the resultant Hz field has no time dependence due to the gradient, and away from this plane, whose orientation is in any selectable direction depending on the gradient coils that are selected, there is an ever increasing time dependent component of Hz. Although the detailed form of the RF excitation pulse sequence is unimportant, it is crucially important that the gradient oscillation frequency be asynchronous with respect to any of the pulse train periodicities. If this is so then the effect of the pulses (wideband) in regions where Hz is varying is to rotate the nuclei through the same angles as in the plane region of constant $H_z$. However between pulses, in regions where $H_z$ is varying the precession rate of the nuclei is continuously varying, and when the next and subsequent pulses occur, there is no coherence in the nuclear behaviour despite the pulse coherence, unlike in the plane region of constant Hz. Thus outside the selected plane, the pulses act in an almost stochastic way to stir up the precession angles of the nuclei in to an incoherent arrangement. The Bloch equations predict then that the net result of this is to saturate these regions provided $1/T_1$, for the nuclei is less than the oscillating gradient frequency (i.e. the nuclei 'remember' the previous gradient field oscillation, because it occurred at time less than $T_1$ ago). Within the selected plane and near it, over a finite thickness where the amplitude of the field excursions is below a certain calculable amount, the effect of the coherent RF excitation pulses is completely ordered and well-behaved, and gives rise to a large and detectable equilibrium N.M.R. response. Signal averaging with repetitive pulse sequences may be used to remove any small time-dependent signals that nevertheless do appear from outside the selected plane, but in practice it is found that the selective saturation phenomenon is so efficient that it is completely unnecessary to arrange for a whole number of oscillating gradients cycles to occupy one N.M.R. signal averaging period.

It is unadvisable however to have a small number of gradient cycles in an averaging period. The 'thickness' of the selected plane is controllable by variation of the amplitude of the oscillating gradient (the current amplitude fed to the gradient-producing coils). The position in space of the selected plane can be moved by arranging that the gradient field is produced by a pair of coil sets, which can be unequally driven so as to move the position of the null plane (where the fields from the two coil sets exactly cancel).

Golay and Helmholtz derived coils are used for the x, y and z gradients respectively. The x and y coil sets are identical and have very similar inductance to the z set. Thus images may be obtained in any plane, in any orientation, of any thickness and in any spatial position—a considerable advantage for example in the precise location of pathology in the head.

A preferred design of the R.F. coil for producing the N.M.R. response is shown in FIG. 16. The coils 20 shown are crossed elliptical or crossed circular coil pairs wound round the tube 22. Crossed ellipses are illustrated but crossed circles can be obtained from them by pulling the cross over points of the two coils 20 off the cylindrical tube 22 till the coils are circular.

Both of these arrangements are found to give the desired good uniformity of field across the patient tube and have a superior filling factor and lower resistance than conventional saddle shaped coils.

Referring now to FIGS. 17 and 18 when a plane has been selected and a selected section has been chosen it is required to rotate round the plane to provide N.M.R. pulses representative of the particular angle. This is accomplished by two preferred methods as illustrated in FIGS. 17 and 18.

In FIG. 17 the power to the coils of the magnets defining the selected section is increased such that the selected section moves continuously and gradually at a relatively slow rate. R.F. pulses are provided at a relatively high pulse repition rate such that for example 200 to 300 pulses are received whilst the gradient angle moves through 1°. Assuming that 200 pulses are received the output of each of the pulses is stored and the average N.M.R. output over the 200 pulses is calculated and used to produce the total N.M.R. picture with averaged pulses from the other angles. FIG. 17 shows in the upper portion the gradually increasing gradient angle and on the lower portion the relatively high frequency R.F. pulses.

In FIG. 18 the preferred alternative method is shown. In this embodiment the x and y coils are supplied with a fixed voltage to maintain the gradient angle fixed for a defined period during which between 200 and 300 R.F. pulses are provided to produce N.M.R. signals from the object being examined. At the end of the fixed period—say 1 second the signals supplied to the x and y coils are incremented and the gradient angle is changed in a step manner through 1° as shown in the upper trace in FIG. 18.

Referring to the centre trace in FIG. 18 it can be seen that there will be distortion of the output response at the time of the step change. To ensure that the disorientation produced is complete a number of pulses of $+90°$, $-90°$, $+90°$, $-90°$ variation are introduced as shown in the lower trace followed by the normal R.F. N.M.R. interrogation pulses. Immediately following the last disorientation pulses the object to be examined begins to recover and the recovery characteristic curve is an indication of $T_1$. Thus the output signals received are sensitive to the $T_1$ values at different points. The average N.M.R. signal is therefore measured over the time period following the early disorientation period.

With reference to FIG. 19 there is shown a block diagram of the major electrical components. The various coils are indicated by boxes for simplicity but they will be as shown in the preceding FIG. 4 etc. Where possible parts if FIG. 19 are given the same reference numerals as in FIG. 5 to indicate the correspondence between the figures. The Central Processing unit 60 runs in time with the reset of the system under the control of a master oscillator and clock generator 62 and the Central Processing Unit 60 controls the system via a data bus 64.

The N.M.R. signal received from the R.F. coil 20 passes via the passive duplex unit 40 to an R.F. receiver 66 which amplifies the signal and feeds the amplified signal to the R.F. phase detector 42. The outputs of the detector 42 are fed to the averager 68 and the outputs of the averager are stored in the storage unit 70.

The N.M.R. picture is formed from the averaged samples of the individual N.M.R. responses as described with reference to FIG. 17 or 18 according to the program sequence shown in FIG. 20. The program is simple and considered mostly self explanatory. The processing within the Central Processing Unit 60 is done in real time whilst the subsequent pulses are delivered to the R.F. coil to produce the next average output.

When all 180° of gradient G have been averaged the process is completed and the program is completed— see exit—and a picture of the plane is displayed. To commence or recommence the programme requires operator control by pressing the start (program enter) button.

We claim:

1. A method of producing an NMR picture of a plane through an object, in which the object is subjected to a high constant magnetic field, to an oscillating magnetic field the intensity of which varies with time in the object except in a selected plane where the oscillating field is substantially zero, and to a magnetic field having a gradient in said plane the orientation of which gradient is varied in accordance with a set program, in which at each position of orientation of the gradient magnetic field the object is subjected to a multiplicity of pulses of RF frequency magnetic radiation including an initial sequence of pulses which saturate the NMR response, and the NMR responses due to the pulses following the initial sequence are averaged and recorded for each position, and in which a picture of total NMR response within the selected plane is obtained by operating on the recorded averaged responses.

2. Apparatus for producing an NMR picture of a plane through an object including a first set of coils for generating a high constant magnetic field, a second set of coils for generating an oscillating magnetic field the intensity of which varies with time in the object except in a selected plane where the oscillating field is substantially zero, and a third set of coils for generating a magnetic field having a gradient in said plane, first control means connected to the third set of coils for generating a set program to control the orientation of the gradient of said gradient magnetic field in said plane in a stepwise manner to produce a step rotation of the gradient orientation, a fourth set of coils for subjecting the object to an RF magnetic field, second control means connected to the fourth set of coils to cause the fourth set of coils to generate a multiplicity of RF pulses at each position of orientation of said gradient magnetic field, each said multiplicity of pulses including an initial sequence of pulses which saturate the NMR response, detection means for detecting and averaging the NMR responses due to the pulses following the initial sequence at each position of orientation of said gradient magnetic field, recording means for recording the averaged NMR responses at each position of orientation of said gradient magnetic field and means for generating from the recorded averaged NMR responses the NMR picture.

3. Apparatus for producing an NMR picture of a plane through an object as claimed in claim 2 in which the first, second and third sets of coils are arranged around a tube within which the object to be examined is placed.

4. Apparatus for producing an NMR picture of a plane through an object as claimed in claim 3 in which the first set of coils comprises four coils wound circumferentially around the tube and spaced along the axis of the tube.

5. Apparatus for producing an NMR picture of a plane through an object as claimed in claim 4 in which the third set of coils comprises a first and second pair of x and a first and a second pair of y coils, the first pair of x and y coils being mounted radially opposite one another in a position on one side of a gap between coils of said first set of coils and the second pair of x and y coils being mounted radially opposite one another on the other side of said gap, the x and y coils being mounted orthogonally with respect to each other to provide magnetic fields at right angles to each other.

6. Apparatus for producing an NMR picture of a plane through an object as claimed in claim 3 in which the fourth set of coils are in the form of a pair of coils arranged around a tube so as to form a crossed pair of coils each of elliptical form surrounding the object and situated in a gap between coils of said first, second and third sets of coils.

7. Apparatus for producing an NMR picture of a plane through an object, as claimed in claim 2, in which the second and third sets of coils are constituted by three sets of coils constructed to produce respectively gradients in three mutually orthogonal directions and to have substantially the same inductance so as to be able to be interchangeably driven by the same pulse generator.

* * * * *